United States Patent
Keshtmand et al.

(10) Patent No.: US 10,953,050 B2
(45) Date of Patent: Mar. 23, 2021

(54) STABLE DRY PROBIOTIC COMPOSITIONS FOR SPECIAL DIETARY USES

(71) Applicant: Advanced BioNutrition Corp., Columbia, MD (US)

(72) Inventors: Majid Keshtmand, Baltimore, MD (US); Mordechai Harel, Pikesville, MD (US); Trisha Rice, Columbia, MD (US)

(73) Assignee: Advanced BioNutrition Corp., Columbia, MD (US)

(*) Notice: Subject to any disclaimer, the term of this patent is extended or adjusted under 35 U.S.C. 154(b) by 156 days.

(21) Appl. No.: 15/747,579

(22) PCT Filed: Jul. 8, 2016

(86) PCT No.: PCT/US2016/041428
§ 371 (c)(1),
(2) Date: Jan. 25, 2018

(87) PCT Pub. No.: WO2017/019273
PCT Pub. Date: Feb. 2, 2017

(65) Prior Publication Data
US 2018/0221422 A1 Aug. 9, 2018

Related U.S. Application Data

(60) Provisional application No. 62/198,220, filed on Jul. 29, 2015.

(51) Int. Cl.
*A23L 33/135* (2016.01)
*A61K 35/747* (2015.01)
(Continued)

(52) U.S. Cl.
CPC .............. *A61K 35/747* (2013.01); *A23L 2/52* (2013.01); *A23L 2/60* (2013.01); *A23L 2/66* (2013.01);
(Continued)

(58) Field of Classification Search
None
See application file for complete search history.

(56) References Cited

U.S. PATENT DOCUMENTS 3,241,977 A 3/1966 Mitchell
3,783,098 A 1/1974 Calnek
(Continued)

FOREIGN PATENT DOCUMENTS

CA 2497264 A1 3/2004
CA 2420095 A1 8/2004
(Continued)

OTHER PUBLICATIONS

Kim et al., J. Vet. Med. Sci., 69(5):535-9 (2007).
(Continued)

*Primary Examiner* — Renee Claytor
*Assistant Examiner* — Trent R Clarke
(74) *Attorney, Agent, or Firm* — RatnerPrestia

(57) ABSTRACT

A dry stable probiotic composition is provided. The composition comprises one or more viable probiotic microorganisms, one or more hydrolyzed proteins, one or more disaccharides, one or more oligosaccharides, and one or more polysaccharides, but not trehalose. The composition has viability of at least $1\times10^{10}$ CFU/g, and a viability loss of less than 1 log unit/g after 3 months at a temperature of 40° C. and a relative humidity of 33%. Also provided are methods for preparing the dry stable probiotic composition.

21 Claims, 1 Drawing Sheet

(51) Int. Cl.
    *A23L 33/00*         (2016.01)
    *A23L 33/18*         (2016.01)
    *A23L 33/185*       (2016.01)
    *A23L 33/125*       (2016.01)
    *A23L 2/52*          (2006.01)
    *A23L 2/66*          (2006.01)
    *A23L 33/15*         (2016.01)
    *A23L 2/60*          (2006.01)
    *A61K 9/00*         (2006.01)
    *A61K 9/14*         (2006.01)
    *A61K 35/745*      (2015.01)

(52) U.S. Cl.
    CPC ........... *A23L 33/125* (2016.08); *A23L 33/135* (2016.08); *A23L 33/15* (2016.08); *A23L 33/18* (2016.08); *A23L 33/185* (2016.08); *A23L 33/40* (2016.08); *A61K 9/0095* (2013.01); *A61K 9/145* (2013.01); *A61K 9/146* (2013.01); *A61K 35/745* (2013.01); *A23V 2002/00* (2013.01); *A23Y 2220/03* (2013.01)

(56) References Cited

U.S. PATENT DOCUMENTS

| | | |
|---|---|---|
| 3,897,307 A | 7/1975 | Porubcan |
| 4,337,242 A | 6/1982 | Markus |
| 4,656,767 A | 4/1987 | Tarrant |
| 5,026,543 A | 6/1991 | Rijke |
| 5,227,373 A | 7/1993 | Alexander et al. |
| 5,262,187 A | 11/1993 | Hahn |
| 5,407,957 A | 4/1995 | Kyle et al. |
| 5,518,918 A | 5/1996 | Barclay |
| 5,637,494 A | 6/1997 | King |
| 5,658,767 A | 8/1997 | Kyle |
| 5,715,774 A | 2/1998 | Adey |
| 5,731,006 A | 3/1998 | Akiyama et al. |
| 5,766,520 A | 6/1998 | Bronshtein |
| 5,908,622 A | 6/1999 | Barclay |
| 5,958,455 A | 9/1999 | Roser et al. |
| 5,968,569 A | 10/1999 | Cavadini et al. |
| 5,981,719 A | 11/1999 | Woiszwillo et al. |
| 6,060,050 A | 5/2000 | Brown |
| 6,187,330 B1 | 2/2001 | Wang et al. |
| 6,190,701 B1 | 2/2001 | Roser et al. |
| 6,258,362 B1 | 7/2001 | Loudon et al. |
| 6,267,958 B1 | 7/2001 | Andya et al. |
| 6,290,991 B1 | 9/2001 | Roser et al. |
| 6,306,345 B1 | 10/2001 | Bronshtein et al. |
| 6,331,310 B1 | 12/2001 | Roser et al. |
| 6,338,856 B1 | 1/2002 | Allen et al. |
| 6,338,866 B1 | 1/2002 | Criggall et al. |
| 6,451,567 B1 | 9/2002 | Barclay |
| 6,468,782 B1 | 10/2002 | Tunnacliffe et al. |
| 6,503,411 B1 | 1/2003 | Franks et al. |
| 6,509,146 B1 | 1/2003 | Bronshtein |
| 6,509,178 B1 | 1/2003 | Tanaka et al. |
| 6,534,087 B2 | 3/2003 | Busson et al. |
| 6,537,666 B1 | 3/2003 | Bronshtein |
| 6,565,871 B2 | 5/2003 | Roser et al. |
| 6,582,941 B1 | 6/2003 | Yokochi et al. |
| 6,586,006 B2 | 7/2003 | Roser et al. |
| 6,589,560 B2 | 7/2003 | Foster et al. |
| 6,664,099 B1 | 12/2003 | Worrall |
| 6,716,460 B2 | 4/2004 | Abril |
| 6,726,934 B1 | 4/2004 | Prokop |
| 6,733,759 B2 | 5/2004 | Ivey et al. |
| 6,790,453 B2 | 9/2004 | Porzio et al. |
| 6,797,266 B2 | 9/2004 | Naidu |
| 6,811,792 B2 | 11/2004 | Roser et al. |
| 6,841,181 B2 | 1/2005 | Jager et al. |
| 6,872,357 B1 | 3/2005 | Bronshtein |
| 6,884,866 B2 | 4/2005 | Bronshtein et al. |
| 6,900,173 B2 | 5/2005 | Martin et al. |
| 6,919,172 B2 | 7/2005 | DePablo et al. |
| 6,964,771 B1 | 11/2005 | Roser et al. |
| 7,005,280 B2 | 2/2006 | Barclay |
| 7,052,719 B2 | 5/2006 | Bernstein et al. |
| 7,056,495 B2 | 6/2006 | Roser et al. |
| 7,122,370 B2 | 10/2006 | Porubcan |
| 7,153,472 B1 | 12/2006 | Bronshtein |
| 7,258,873 B2 | 8/2007 | Truong-Le |
| 7,282,194 B2 | 10/2007 | Sung et al. |
| 7,381,425 B1 | 6/2008 | Truong-Le |
| 7,396,548 B2 | 7/2008 | Kyle |
| 7,744,925 B2 | 6/2010 | Roser et al. |
| 7,842,310 B2 | 11/2010 | Hwang et al. |
| 7,927,858 B2 | 4/2011 | Mayeresse |
| 7,939,105 B2 | 5/2011 | Parikh et al. |
| 7,998,502 B2 | 8/2011 | Harel |
| 8,097,245 B2 | 1/2012 | Harel |
| 8,377,496 B2 | 2/2013 | Clinger et al. |
| 8,460,726 B2 | 6/2013 | Harel |
| 8,834,951 B2 | 9/2014 | Harel et al. |
| 8,871,266 B2 | 10/2014 | Crittenden et al. |
| 8,968,721 B2 | 3/2015 | Harel |
| 9,044,497 B2 | 6/2015 | Harel |
| 9,072,310 B2 | 7/2015 | Harel |
| 10,370,636 B2 | 8/2019 | Van Hee |
| 2001/0012610 A1 | 8/2001 | Bronshtein |
| 2001/0016220 A1 | 8/2001 | Jager et al. |
| 2002/0192202 A1 | 12/2002 | Naidu |
| 2003/0017192 A1 | 1/2003 | Kanafani et al. |
| 2003/0022333 A1 | 1/2003 | Bronshtein |
| 2003/0147898 A1 | 8/2003 | Van Nest et al. |
| 2003/0165472 A1 | 9/2003 | McGrath et al. |
| 2003/0190332 A1 | 10/2003 | Gilad et al. |
| 2004/0038825 A1 | 2/2004 | Leland et al. |
| 2004/0047881 A1 | 3/2004 | Kyle |
| 2004/0062758 A1 | 4/2004 | Mayra-Makinen et al. |
| 2004/0081638 A1 | 4/2004 | Kyle |
| 2004/0081699 A1 | 4/2004 | Rademacher et al. |
| 2004/0175389 A1 | 9/2004 | Porubcan |
| 2004/0177392 A1 | 9/2004 | Barratt et al. |
| 2004/0219206 A1 | 11/2004 | Roser et al. |
| 2004/0241313 A1 | 12/2004 | Nana |
| 2005/0019417 A1 | 1/2005 | Ko et al. |
| 2005/0032192 A1 | 2/2005 | Vesey |
| 2005/0079244 A1 | 4/2005 | Giffard |
| 2005/0100559 A1 | 5/2005 | Myatt et al. |
| 2005/0123599 A1 | 6/2005 | Ott et al. |
| 2005/0153018 A1 | 7/2005 | Ubbink et al. |
| 2005/0241011 A1 | 10/2005 | Allnut |
| 2005/0266069 A1 | 12/2005 | Simmons et al. |
| 2006/0008861 A1 | 1/2006 | Allnutt |
| 2006/0024404 A1 | 2/2006 | Kyle |
| 2006/0051408 A1 | 3/2006 | Parente Duena et al. |
| 2006/0120999 A1 | 6/2006 | Dhar |
| 2006/0121468 A1 | 6/2006 | Allnutt |
| 2006/0127453 A1 | 6/2006 | Harel |
| 2006/0130162 A1 | 6/2006 | Kyle |
| 2006/0147500 A1 | 7/2006 | Klingeberg |
| 2006/0154067 A1 | 7/2006 | Cooper |
| 2006/0222694 A1 | 10/2006 | Oh |
| 2006/0258623 A1 | 11/2006 | Harel et al. |
| 2006/0265766 A1 | 11/2006 | Kyle et al. |
| 2007/0020289 A1 | 1/2007 | Mattern |
| 2007/0031534 A1 | 2/2007 | Tsujimoto et al. |
| 2007/0082008 A1 | 4/2007 | Harel et al. |
| 2007/0122397 A1 | 5/2007 | Sanguansri et al. |
| 2007/0196508 A1 | 8/2007 | Heuer et al. |
| 2007/0207165 A1 | 9/2007 | Thiry et al. |
| 2007/0211397 A1 | 9/2007 | Sokolow |
| 2007/0292952 A1 | 12/2007 | Dhar |
| 2008/0044081 A1 | 2/2008 | Lieb |
| 2008/0044481 A1 | 2/2008 | Harel |
| 2008/0050497 A1 | 2/2008 | Mai |
| 2008/0102132 A2 | 5/2008 | Giner et al. |
| 2008/0107634 A1 | 5/2008 | Mogna et al. |
| 2008/0112972 A1 | 5/2008 | Truong-Le |
| 2008/0131514 A1 | 6/2008 | Truong-Le |
| 2008/0193546 A1 | 8/2008 | Roser et al. |
| 2008/0194504 A1 | 8/2008 | Kyle et al. |

(56) References Cited

U.S. PATENT DOCUMENTS

| | | |
|---|---|---|
| 2008/0221231 A1 | 9/2008 | Cooper et al. |
| 2008/0229609 A1 | 9/2008 | Bronshtein |
| 2008/0241244 A1 | 10/2008 | Truong-Le |
| 2008/0261916 A1 | 10/2008 | Jaszberenyi |
| 2009/0155351 A1 | 6/2009 | Hejl et al. |
| 2009/0162518 A1 | 6/2009 | Clinger et al. |
| 2009/0162521 A1 | 6/2009 | Clinger et al. |
| 2009/0181363 A1 | 7/2009 | Dhar |
| 2009/0203592 A1 | 8/2009 | Beermann et al. |
| 2009/0208585 A1 | 8/2009 | Roser et al. |
| 2009/0232894 A1 | 9/2009 | Chouvenc |
| 2009/0238890 A1 | 9/2009 | Piechocki |
| 2009/0246184 A1 | 10/2009 | Harel |
| 2009/0324636 A1 | 12/2009 | Piechocki |
| 2010/0015177 A1 | 1/2010 | Drew |
| 2010/0047393 A1 | 2/2010 | Glas et al. |
| 2010/0074994 A1 | 3/2010 | Harel |
| 2010/0086638 A1 | 4/2010 | Kyle et al. |
| 2010/0092521 A1 | 4/2010 | Dhar et al. |
| 2010/0120014 A1 | 5/2010 | Bronshtein |
| 2010/0120676 A1 | 5/2010 | Boehm et al. |
| 2010/0189767 A1 | 7/2010 | Shimoni et al. |
| 2010/0242301 A1 | 9/2010 | Rampersad et al. |
| 2010/0297231 A1 | 11/2010 | Vehring |
| 2011/0070334 A1 | 3/2011 | Rangavajla |
| 2011/0120489 A1 | 5/2011 | Pye |
| 2011/0223282 A1 | 9/2011 | Bergonzelli Degonda et al. |
| 2012/0009248 A1 | 1/2012 | Truong-Le |
| 2012/0039956 A1 | 2/2012 | Harel |
| 2012/0040010 A1 | 2/2012 | Harel |
| 2012/0114621 A1 | 5/2012 | Harel |
| 2012/0135017 A1 | 5/2012 | Harel et al. |
| 2012/0288483 A1 | 11/2012 | Harel |
| 2012/0322663 A1 | 12/2012 | Harel et al. |
| 2013/0287896 A1 | 10/2013 | Harel et al. |
| 2013/0296165 A1 | 11/2013 | Harel et al. |
| 2013/0344045 A1 | 12/2013 | Faure et al. |
| 2014/0093613 A1 | 4/2014 | Cevallos et al. |
| 2014/0255366 A1 | 9/2014 | Yde |

FOREIGN PATENT DOCUMENTS

| | | |
|---|---|---|
| CA | 2 807 997 A1 | 2/2012 |
| CL | 0931-2008 | 3/2008 |
| CN | 1223865 A | 7/1999 |
| CN | 101287449 A | 10/2008 |
| CN | 101951789 A | 1/2011 |
| CN | 102186360 A | 9/2011 |
| CN | 103249830 A | 8/2013 |
| CN | 103347395 A | 10/2013 |
| EP | 0 028 563 A1 | 5/1981 |
| EP | 0 259 739 A1 | 3/1988 |
| EP | 0 471 904 A1 | 2/1992 |
| EP | 1 110 462 A2 | 6/2001 |
| EP | 1 344 458 A1 | 9/2003 |
| GB | 1 232 057 A | 5/1971 |
| GB | 2 389 787 A | 12/2003 |
| JP | 57114527 A | 7/1982 |
| JP | 05246856 A | 9/1993 |
| JP | 0622746 A | 2/1994 |
| JP | 11506467 A | 6/1999 |
| JP | 11513700 A | 11/1999 |
| JP | 2001505431 A | 4/2001 |
| JP | 2002512970 A | 5/2002 |
| JP | 2002530321 A | 9/2002 |
| JP | 2004506437 A | 3/2004 |
| JP | 2004525106 A | 8/2004 |
| JP | 2004528288 A | 9/2004 |
| JP | 2005501268 A | 1/2005 |
| JP | 2005519600 A | 7/2005 |
| JP | 2005270100 A | 10/2005 |
| JP | 2005534741 A | 11/2005 |
| JP | 2007519796 A | 7/2007 |
| JP | 2007522085 A | 8/2007 |
| JP | 2009522280 A | 6/2009 |
| JP | 2010512755 A | 4/2010 |
| JP | 2010227125 A | 10/2010 |
| JP | 2013535222 A | 9/2013 |
| JP | 2015517985 A | 6/2015 |
| KR | 20050105669 A | 11/2005 |
| KR | 20050106559 A | 11/2005 |
| RU | 2277905 C2 | 6/2006 |
| RU | 2374859 C2 | 12/2009 |
| RU | 2410084 C1 | 1/2011 |
| WO | 95_27721 A1 | 10/1995 |
| WO | 96_40077 A2 | 12/1996 |
| WO | 98_24327 A1 | 6/1998 |
| WO | 98_24882 A1 | 6/1998 |
| WO | 00_32064 A1 | 6/2000 |
| WO | 01_12779 A1 | 2/2001 |
| WO | 01_36590 A1 | 5/2001 |
| WO | 02_15720 A2 | 2/2002 |
| WO | 02_058735 A1 | 8/2002 |
| WO | 02_061111 A2 | 8/2002 |
| WO | 02_076391 A2 | 10/2002 |
| WO | 03_086454 A1 | 10/2003 |
| WO | 03_087327 A2 | 10/2003 |
| WO | 03_088755 A1 | 10/2003 |
| WO | 03_089579 A2 | 10/2003 |
| WO | 03_103692 A1 | 12/2003 |
| WO | 2004022728 A1 | 3/2004 |
| WO | 2004024177 A1 | 3/2004 |
| WO | 2004039417 A2 | 5/2004 |
| WO | 2004043139 A2 | 5/2004 |
| WO | 2004080196 A2 | 9/2004 |
| WO | 2004091307 A2 | 10/2004 |
| WO | 2004112767 A1 | 12/2004 |
| WO | 2004112776 A2 | 12/2004 |
| WO | 2005030229 A1 | 4/2005 |
| WO | 2005060937 A1 | 7/2005 |
| WO | 2005084646 A1 | 9/2005 |
| WO | 2005105978 A2 | 11/2005 |
| WO | 2005115341 A2 | 12/2005 |
| WO | 2005117962 A1 | 12/2005 |
| WO | 2006085082 A1 | 8/2006 |
| WO | 2006122299 A2 | 11/2006 |
| WO | 2007035455 A2 | 3/2007 |
| WO | 2007038926 A1 | 4/2007 |
| WO | 2007067207 A1 | 6/2007 |
| WO | 2007075988 A2 | 7/2007 |
| WO | 2007079147 A2 | 7/2007 |
| WO | 2007084059 A1 | 7/2007 |
| WO | 2007084500 A2 | 7/2007 |
| WO | 2007117511 A2 | 10/2007 |
| WO | 2007136553 A2 | 11/2007 |
| WO | 2008016214 A1 | 2/2008 |
| WO | 2008056983 A1 | 5/2008 |
| WO | 2008076975 A1 | 6/2008 |
| WO | 2009002481 A1 | 12/2008 |
| WO | 2009020455 A1 | 2/2009 |
| WO | 2009140327 A2 | 11/2009 |
| WO | 2010002418 A2 | 1/2010 |
| WO | 2010046321 A1 | 4/2010 |
| WO | 2010111347 A2 | 9/2010 |
| WO | 2010118188 A2 | 10/2010 |
| WO | 2010118205 A3 | 10/2010 |
| WO | 2010125084 A1 | 11/2010 |
| WO | 2010135495 A2 | 11/2010 |
| WO | 2010138522 A2 | 12/2010 |
| WO | 2011094469 A2 | 8/2011 |
| WO | 2012021783 A2 | 2/2012 |
| WO | 2013142792 A1 | 9/2013 |

OTHER PUBLICATIONS

Korean Office Action for Korean Application No. 10-2011-7031038, dated Dec. 27, 2016.
Krallish et al., Appl. Microbiol Biotechnol., 47:447-51 (1997).
Krasaekoopt et al., International Dairy Journal, 13:3-13 (2003).
Kumar et al., Fish & Shell Immunology, 25(1-2):47-56 (2008).
Le Meste, et al., Journal of Food Science, 67:2444-58 (2002).
Li et al., BMC Biotechnology, 8(89):1-11 (2008).
Liao et al., Pharmaceutical Research, 19(12):1854-61 (2002).

(56) References Cited

OTHER PUBLICATIONS

Linders et al., Cryobiology, 35:31-40 (1997).
Malik et al., Curr. Drug Deliv., 4(2):141-51 (2007).
Maltrin M100 Maltodrexin, 2006, XP055120984, Internet retrieves from the Internet: URL: http://www.tpipremixes.com/productpdfs/Maltodextrin.pdf, retrieved on Jun. 2, 2014.
Marteau et al., Am J Clin Nutr., 73:430S-436S (2001).
Martinez, Neurology, 40:1292-8 (1990).
Mazur et al., Macromolecules, 47:771-6 (2014).
Mexican Office Action for Mexican Application No. MX/a/2012/008795 dated Jul. 20, 2015.
Mexican Office Action for Mexican Application No. MX/a/2013/001535, dated Jul. 13, 2016.
Mexican Office Action for Mexican Application No. MX/a/2013/001535, dated Nov. 29, 2016.
Miao et al., Daily Science and Technology, 88(1):19-30 (2008).
Morgan, Journal of Microbiological Methods, 66:183-93 (2006).
New Zealand Examination Report for New Zealand Application No. 597053 dated May 18, 2012.
New Zealand Office Action for New Zealand Application No. 628912 dated Jun. 24, 2015.
Niness, Nutr., 129:1402S-1406S (1999).
Non Final Office Action dated Jan. 22, 2016 for U.S. Appl. No. 13/321,708.
Non Final Office Action for U.S. Appl. No. 14/644,248, dated Jul. 15, 2016.
Non Final Office Action dated Feb. 3, 2016 for U.S. Appl. No. 14/456,130.
Non-Final Office Action dated Jun. 8, 2018 for U.S. Appl. No. 15/269,171.
Non-Final Office Action dated Oct. 27, 2015 in U.S. Appl. No. 13/208,459.
Notice of Allowance dated Jan. 15, 2015 in U.S. Appl. No. 13/911,636.
Notice of Allowance dated Oct. 27, 2014 in U.S. Appl. No. 13/459,408.
Notification of Reexamination of Chinese Application No. 201080029392.4, dated Jul. 13, 2016.
Office Action for Chinese Application No. 201380015928.0, dated Nov. 3, 2017.
Office Action for Patent Application JP 2009-541634 dated Jun. 25, 2012.
Office Action for Russian Application No. 2011151788/10(077759) dated Mar. 21, 2014.
Office Action for Russian Application No. 2011151788/10(077759) dated Dec. 18, 2014.
Office Action for Russian Application No. 2013110833/13(016008) dated Jul. 21, 2015.
Office Action for Russian Application No. 2014136089, dated May 17, 2017.
Iaconelli et al., Journal of Biotechnology, 214:17-26 (2015).
Office Action for Russian Patent Application No. 2014136089, dated Feb. 14, 2018.
Office Action for Russian Application No. 2011151788/10 (077759) dated Aug. 6, 2014.
Office Action in U.S. Appl. No. 15/269,171 dated Oct. 16, 2017.
Final Office Action dated Jan. 14, 2015 in U.S. Appl. No. 13/321,708.
Final Office Action dated Oct. 27, 2014 in U.S. Appl. No. 13/208,459.
Office Action dated Jun. 30, 2015 in Vietnamese Application No. 1-2011-03487.
Panos et al., Current Drug Discovery Technologies, 5:333-41 (2008).
Perdigon et al, Curr Issues Intest Microbiol., 2:27-42 (2001).
Perry, Molecular Biotechnology, 9(1):59-64 (1998).
Philippine Office Action dated Jan. 14, 2016 for Philippine Application No. 1-2011-502445.
Philippines Substantive Examination Report dated Apr. 15, 2016 for Philippines Application No. 1-2012-501410.
Qiu et al., Comparative Biochemistry & Physiology, Part B, 125:411-9 (2000).
Rege et al., International Journal of Pharmaceutics 252:41-51 (2003).
International Preliminary Report on Patentability and Written Opinion for International Application No. PCT/US2016/041428, dated Jan. 30, 2018, 10 pages.
Bakker-Zierikzee et al., British Journal of Nutrition, 94(5):783-90 (2005).
International Search Report for PCT Application No. PCT/US2016/041428 dated Oct. 21, 2016.
Sanchez et al., Intl. J. Pharm., 185:255-66 (1999).
Santivarangkna et al., Journal of Food Science, 76(8):R152-R-156 (2011).
Schwab et al., Cryobiology, 55:108-14 (2007).
Second Office Action issued by the State Intellectual Property Office of the Peoples Republic of China Feb. 8, 2014 in Chinese Application No. 2011800756.3, including a Search Report.
Selmer-Olsen et al., Journal of Industrial Microbiology & Biotechnology, 23:79-85 (1999).
Shah, Journal Dairy Sci., 83:894-907 (2000).
Shin et al., Journal of Food Science, 65(5):884-7 (2000).
Shiraishi et al., Journal of Controlled Release, 25:217-25 (1993).
Shu et al., International Journal of Pharmaceutics, 201:51-58 (2000).
Singapore Search Report and Written Opinion for Application No. 11201405478V dated Sep. 9, 2015.
Stordy, Lancet, 346(8971):385, 2 pages (1995).
Substantive Examination Adverse Report for Malaysian Application No. PI 2011005733 dated Aug. 29, 2014.
Substantive Examination Adverse Report for Malaysian Application No. PI 2011005733 dated Jun. 30, 2015.
Substantive Examination Adverse Report for Malaysian Application No. PI 2013000306 dated Sep. 15, 2015.
Substantive Examination Report for Philippines Application No. 1-2014-502092 dated Feb. 6, 2018.
Substantive Examination Report II for Indonesia Patent Application No. W00201300512 dated Mar. 8, 2018.
Sucrose, Sucrose structure, Webpage, Elmhurst College (2003).
Supplementary European Search Report dated Sep. 18, 2013 for European Appl. No. 11737688.9.
Supplementary European Search report in European Application No. EP 10781100.2-2405 dated Oct. 9, 2012.
Tian et al., Veterinary Immunology and Immunopathology, 126(3-4):220-9 (2008).
Tobar et al., World Aquaculture Society's 2008 Annual International Conference (May 19-23, 2008).
van der Lubben et al., Advanced Drug Delivery Reviews, 52(2):139-44 (2001).
van der Lubben et al., Biomaterials, 22(7):687-94 (2001).
Wong, Recent Patents on Drug Delivery & Formation, 3(1):8-25 (2009).
Xu et al., J Biol Chem, 271:24711-9 (1996).
Zarate et al., Process Biochemistry, 41:1779-85 (2006).
Zhou et al., Journal of Controlled Release, 86:195-205 (2003).
Higl et al., Biotechnol. Prog., 23:794-800 (2007).
Kurtmann et al., Biotechnol. Prog., 25(1):265-70 (2009).
Kurtmann et al., "The Browning of Freeze-Dried Probiotic Bacteria Cultures and Its Relation to the Loss of Viability During Storage", University of Copenhagen, 30 pages (2009).
Kurtmann et al., Cryobiology, 58:175-80 (2009).
Nazzaro et al., Journal of Functional Foods I, pp. 319-323 (2009).
Harel and Tang, "A Novel Preservation and Delivery Technology for Live Probiotics, Enzymes and Vitamins", XVIIth International Conference on Bioencapsulation, 2 pages (Sep. 24-26, 2009).
Carlsen et al., Cryobiology, 6 pages (2009).
Japanese Office Action dated Aug. 1, 2014 for Japanese Application No. 2012-513183, 9 pages.
Non-Final Office Action dated Jan. 12, 2016 for U.S. Appl. No. 14/479,791.
Canadian Office Action for Canadian Application No. 2,763,074, dated Oct. 22, 2018, 4 pages.
Communication of Notice of Opposition of EP Application No. 10781100.2, dated Apr. 26, 2018, 34 pages.
Communication of Notice of Opposition of EP Application No. 10781100.2, dated May 23, 2014, 1 page.

(56) References Cited

OTHER PUBLICATIONS

Kurtman, "Viability of Dried Lactic Acid Bacteria: Relation Between Physical State of Freeze-Drying", Thesis by Lone Kurtman, 69 pages (2009).
Final Office Action for U.S. Appl. No. 13/321,708, dated Jul. 5, 2018, 20 pages.
Substantive Examination Report for Philippines Application No. 1-2014-502092, dated Jun. 14, 2019—4 pages.
Korean Office Action for Korean Application No. 10-2024-7029648, dated Jun. 11, 2019, with translation—20 pages.
Final Office Action for U.S. Appl. No. 15/687,730, dated Jun. 24, 2019—21 pages.
Australian Examination Report for Australian Application No. 2016297986, dated Sep. 30, 2019, 3 pages.
Esquisabel et al., J. Microencapsulation, 24:627-38 (1997).
European Communication for European Application No. 07865743.4 dated Mar. 2, 2017.
European Examination Report for EP Application No. 11817090.1 dated Jul. 15, 2016.
European Office Action for Application No. 10 781 100.2-1403 dated Oct. 17, 2014.
European Office Action for European Application No. 10756894.1 dated Jun. 22, 2016.
European Office Action for European Application No. 11817090.1 dated Nov. 6, 2015.
Examination Report for Chilean Application No. 201402506 dated Oct. 16, 2017.
Examination Report for India Application No. 824/DELNP/2013, dated Oct. 18, 2017.
Examination Report for Indonesia Application No. W-00201202694, dated Nov. 27, 2017.
Examination Report on Patent Application for Chilean Application No. 759-09 dated Mar. 27, 2009.
Extended European Search Report for European Application No. 11817090.1-1358 dated Jun. 16, 2014.
Extended European Search Report for European Application No. 13764138.7-1460 dated Apr. 9, 2015.
Favaro-Trindade et al., J. Microencapsulation, vol. 19, pp. 485-94 (2002).
Final Office Action for U.S. Appl. No. 13/260,661, dated Jun. 1, 2016, 47 pages.
Final Office Action for U.S. Appl. No. 13/321,708, dated Aug. 5, 2016, 30 pages.
First Examination Report for Indian Patent Application No. 7257/DELNP/2012, dated Jan. 11, 2018 (with English Translation).
First Office Action with a Search Report for Chinese Application No. 201180007562.3, issued by the State Intellectual Property Office of the People's Republic of China dated May 22, 2013.
Grinstead et al., Animal Feed Sci Technol, 83:237-47 (2000).
He et al., J Animal Physiol Animal Nutri, 86:97-104 (2002).
Hincha et al., European Biophysics Journal, 37:503-8 (2008).
Huang et al., Journal of Microencapsulation, 20(2):247-60 (2003).
Hughes and Hillier, Obstet Gynecol., 75:244-8 (1990).
Ikemoto et al., Neurochem Res, 22:671-8 (1997).
India Office Action for India Application No. 9996/DELNP/2011, dated Sep. 12, 2017.
Indonesian Examination Report for Indonesian Application No. W00 2013 00512, dated Jun. 30, 2016.
Indonesian Examination Report for Indonesian Application No. W00 201104583, dated Jun. 27, 2016, 4 pages.
International Preliminary Report on Patentability and Written Opinion for PCT International Application No. PCT/US2013/033505 dated Sep. 23, 2014.
International Preliminary Report on Patentability for PCT International Application No. PCT/US2011/022821 dated Jul. 31, 2012.
International Search Report for Application No. PCT/US2010/028767 dated Dec. 23, 2010.
International Search Report for International Application No. PCT/US2010/036098 dated Feb. 14, 2011.
International Search Report for International Application No. PCT/US2011/022821 dated Oct. 25, 2011.
International Search Report for International Application No. PCT/US2006/49434 dated Sep. 26, 2007.
International Search Report for International Application No. PCT/US2007/087771 dated May 16, 2008.
Isolauri et al., Am J Clin Nutr., 73:444S-450S (2001).
Japanese Office Action for Japanese Application No. 2012-513183 dated Mar. 31, 2015.
Japanese Office Action for Japanese Application No. 2009-541634 dated Jun. 25, 2012.
Japanese Office Action for Japanese Application No. 2012-513183 dated Sep. 11, 2015.
Japanese Office Action for Japanese Application No. 2012-551295 dated Mar. 2, 2015.
Japanese Office Action for Japanese Application No. 2012-551295 dated Oct. 7, 2015.
Japanese Office Action for Japanese Patent Application No. 2008-548729, dated Jul. 23, 2012.
Japanese Office Action issued in Japanese Application No. 2013-524242, dated Jan. 21, 2014.
Kailasapathy et al., Immunology Cell Biology, 78:80-8 (2000).
Kang et al., Vaccine 25:4602-10 (2007).
Kearney, et al., Applied and Environmental Microbiology, 56(10):3112-6 (1990).
Kets et al., Cryobiology, 48:46-54 (2004).
Abdelwahed et al., Advanced Drug Delivery Reviews, 58:1688-1713 (2006).
Anal et al., Trends in Food Science and Technology, 18(5):240-51 (2007).
Anderson et al., Am J Clin Nutr, 70:525-35 (1999).
Annear, J. Gen. Microbiol., 27:341-3 (1962).
Aral et al., International Journal of Pharmaceutics 168:9-15 (1998).
Australian Examination Report for Australian Application No. 2013234931, dated Dec. 7, 2016, 4 page.
Australian Examination Report for Australian Application No. 2013234931, dated Mar. 21, 2017, 3 page.
Australian Patent Examination Report in Patent Application No. 2010254235, dated Jan. 23, 2015.
Bazan and Rodriguez, J. Ocul Pharmacol, 10:591-604 (1994).
Bazan and Scott, Upsala J Med Sci, Suppl, 48:97-107 (1990).
Behrens and Kyle, J Food Sci, 3:259-72 (1996).
Benedict et al., Appl. Microbiol., 6(6):401-7 (1958).
Bergogne et al., Molecular Crystals and Liquid Crystals, 354: 79-89 (2000).
Bodmeier et al., Drug Development and Industrial Pharmacy, 15(9):1475-94 (1989).
Boswell et al., SCO Production by Fermentive Microalgae. In: Kyle DJ, Ratledge C (eds) Industrial Applications of Single Cell Oils. American Oil Chemists Society, Champaign, IL., pp. 274-286 (1992).
Bradford, Analytical biochemistry 72:248-54 (1976).
Calvo et al., Journal of Applied Polymer Science, 63:125-32 (1997).
Canadian Office Action for Canadian Application No. 2,673,120, dated Apr. 6, 2011.
Canadian Office Action for Canadian Application No. 2,756,883, dated Sep. 9, 2016.
Canadian Office Action for Canadian Application No. 2,756,883, dated Dec. 8, 2015.
Canadian Office Action for Canadian Application No. 2,763,074, dated Mar. 10, 2016.
Canadian Office Action for Canadian Application No. 2,785,815, dated Oct. 14, 2016.
Canadian Office Action for Canadian Application No. 2,785,815, dated Oct. 10, 2014.
Canadian Office Action for Canadian Application No. 2,785,815, dated Sep. 8, 2015.
Capela et al., Food Research International 39:203-11 (2006).
Chen et al., China Tropical Medicine, 7(4):654-55 (2007) (with partial English translation).
Chen et al., Cryobiology, 43:168-81 (2001).
Chilean Examination Report for Application No. 2506-14 dated Jan. 24, 2017.

(56) References Cited

OTHER PUBLICATIONS

Chinese Office Action for Chinese Application No. 201180007562.3 dated Mar. 2, 2015.
Chinese Office Action for Chinese Application No. 201380015928.0 dated Feb. 26, 2016.
Chinese Office Action for Chinese Application No. 201380015928.0 dated Apr. 5, 2017.
Chinese Office Action for Chinese Application No. 201410326898.1 dated Apr. 1, 2016.
Chinese Reexamination Report for Chinese Application No. 201080029392.4 dated Dec. 23, 2015.
Chinese Search Report for Chinese Application No. 201180039219.7 dated May 26, 2014.
Chinese Search Report for Chinese Application No. 2013800115928.0 dated Feb. 23, 2016.
Chopra et al., J. Pharm. Pharmacol., 58(8):1021-32 (2006).
Crawford et al., Eur J. Pediatr, 157(Suppl 1):S23-7 (1998).
Crowe et al., Adv. Space Res, 12(4):239-47 (1992).
Crowe et al., Cryobiology, 20:346-56 (1983).
Crowe, Annu. Rev. Physiol., 60:73-103 (1998).
Dang et al., Adv. Drug Deliv. Rev., 58(4):487-99 (2006).
Davis, Vaccine, 24(2):7-10 (2006).
De Giulio, et al., World Journal of Microbiology and Biotechnology, 21(5):739-46 (2005).
Desai et al. Pharmaceutical Research, 1(12):1838-45 (1996).
Japanese Notice of Reasons for Rejection for Japanese Application No. 2018-504716, dated Jan. 28, 2020 with translation, 10 pages.
Chinese Office Action for Chinese Application No. 201680051904.4, dated Oct. 16, 2020 with partial translation, 16 pages.
Argentine Office Action for Argentine Application No. P160102257, dated Sep. 2, 2020 with partial translation, 6 pages.
Notice of Reasons for Rejection for Japanese Application No. 2018-504716, dated Dec. 8, 2020, with translation, 6 pages.

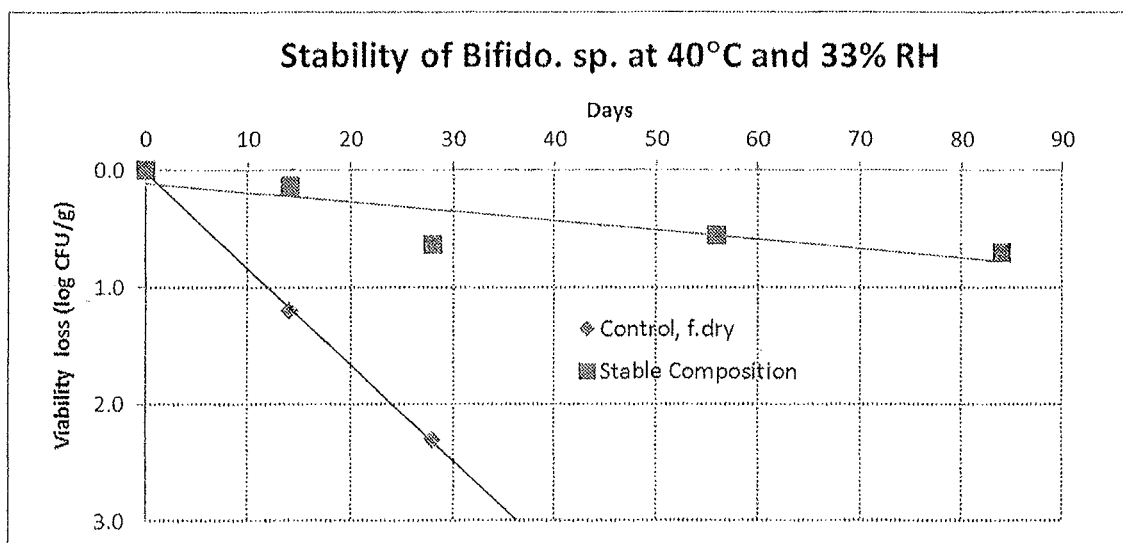

STABLE DRY PROBIOTIC COMPOSITIONS FOR SPECIAL DIETARY USES

This application is a U.S. National Phase Application of PCT International Application PCT/US2016/041428, filed Jul. 8, 2016, related to and claims the benefit of U.S. Provisional Application No. 62/198,220, entitled STABLE DRY PROBIOTIC COMPOSITIONS FOR SPECIAL DIETARY USES filed on Jul. 29, 2015, the contents of each of which are incorporated herein by reference.

FIELD OF THE INVENTION

The present invention relates to stable probiotic compositions for special dietary uses, for example, an infant formula.

BACKGROUND OF THE INVENTION

There are currently a variety of probiotic microorganisms (also called probiotics) for supplementing gastrointestinal tracts of animals, including humans. These microorganisms may modulate a natural microflora within an animal's gut for a desirable biological effect.

One of the challenges to providing an effective amount of probiotic bacteria to a host is the preservation of their viability under the harsh conditions of typical industrial manufacturing processes and long-term storage at high temperature and humidity. Although there have been developments concerning encapsulation and formulation techniques for delivery of biological materials into digestive systems of animals, there has been little development in encapsulation or stabilization techniques that protect the viability of probiotics during manufacturing processes, distribution and storage. There is a need for a stabilization technique that enables probiotic bacteria to survive upon exposure to various harsh environments, especially those associated with elevated temperature and humidity.

In addition, the inherent moisture of a probiotic product itself poses another challenge in that probiotics generally are sensitive to water activity, especially in combination with high temperature. To date, no technology or technique has been identified to provide significant protection of probiotics under intermediate moisture conditions (i.e., water activity of about 0.2 and higher, or up to about 0.4 or higher) and high temperatures during distribution and storage (e.g., temperatures of at least about 30° C., or up to about 40° C. or higher) when incorporated into products such as nutritional products. As such, there is a need for stable probiotic compositions suitable for distribution in various geographic locations, including those in tropical climates, where the viability of probiotics could be compromised.

Additional challenges include regulatory limitations on the use of conventional food ingredients in special dietary formulations suitable for consumption by people like infants, young children and elderly people. Conventional synthetic encapsulation and stabilizing compounds and even some natural compounds such as gum acacia, alginate, milk proteins and certain sugars such as trehalose are not recommended for use in these special dietary formulations. A recommended list of nutritional compounds allowed for special dietary uses is regulated by the joint FAO/WHO Codex Alimentarius Commission.

What is desired therefore are stable probiotic compositions suitable for special dietary uses comprising probiotic microorganisms such as probiotic bacteria and other ingredients and stabilization techniques for making such compositions.

SUMMARY OF THE INVENTION

The present invention provides stable dry probiotic compositions for special dietary uses and their preparation methods.

According to one aspect of the invention, a dry composition is provided. The composition comprises one or more viable probiotic microorganisms, one or more hydrolyzed proteins, one or more disaccharides, one or more oligosaccharides, and one or more polysaccharides. The composition does not comprise trehalose. The composition has viability of at least $1 \times 10^1$ CFU/g, a viability loss of less than 1 log unit/g after 3 months at a temperature of 40° C. and a relative humidity of 33%.

The composition may provide a probiotic benefit to a host in a special dietary product. The special dietary product may be selected from the group consisting of an infant formula, a follow-on formula, processed cereal based food, canned baby food, an animal supplement or treatment, and/or a special food for a medical purpose. In particular embodiments, the special dietary product is an infant formula.

The viable probiotic microorganism may be selected from the group consisting of live probiotic bacteria, fungi, and yeast.

The composition may comprise at least 50% of the one or more hydrolyzed proteins, based on the total dry weight of the composition. The one or more hydrolyzed proteins may be selected from the group consisting of milk proteins, plant proteins, and combinations thereof. The one or more hydrolyzed proteins may be selected from the group consisting of hydrolyzed casein, hydrolyzed whey protein, hydrolyzed pea protein, hydrolyzed soy protein, and combinations thereof.

The composition may comprise less than 20% of the one or more disaccharides, based on the total dry weight of the composition. The one or more disaccharides may be selected from the group consisting of sucrose, lactose, and combinations thereof.

The composition may comprise 5-30% of the one or more oligosaccharides, based on the total dry weight of the composition. The one or more oligosaccharides may be selected from the group consisting of inulin, maltodextrins, dextrans, fructo-oligosaccharides (FOS), galacto-oligosaccharides (GOS), mannan-oligosaccharides (MOS), and combinations thereof.

The composition may comprise 1-10% of the one or more polysaccharides, based on the total dry weight of the composition. The one or more polysaccharides may be selected from the group consisting of carrageenan, guar gum, gum acacia, locust bean gum, starches, modified starches, and combinations thereof.

The composition may further comprise one or more additional agents. The composition may comprise 0.5-10% of the one or more additional agents, based on the total weight of the composition. The one or more additional agents may be selected from the group consisting of carboxylic acid salts, tocopherols, and combinations thereof. The carboxylic acid salts may be selected from the group consisting of ascorbic acid salts and citric acid salts. The one or more additional agents may comprise one or more tocopherols and one or more carboxylic acid salts at a weight ratio from 1:4 to 4:1. Preferably, the one or more additional agents comprise vitamin E and sodium ascorbate at a weight ratio of 4:1.

According to another aspect of the invention, a method for preparing the composition of the present invention is provided. The method comprises one or more drying processes selected from the group consisting of air drying, vacuum-drying, fluid bed drying and spray-drying.

According to yet another aspect of the invention, a method for preparing the composition of the present invention is provided. The method comprises: (a) combining the one or more viable probiotic microorganisms, the one or more hydrolyzed proteins, the one or more disaccharides, the one or more oligosaccharides, and the one or more polysaccharides in an alkali aqueous solvent to form a slurry; (b) snap-freezing the slurry in liquid nitrogen to form solid frozen particles in the form of beads, droplets or strings; (c) primary drying step of the solid frozen particles by evaporation, under vacuum, while maintaining the temperature of the particles above their freezing temperature, whereby a primarily dried formulation is formed; and (d) secondary drying of the primarily dried formulation at full strength vacuum and a heat source temperature of 20° C. or higher for a time sufficient to reduce the water activity of the primarily dried formulation to 0.3 Aw or lower. As a result, the composition of the invention is prepared. The method may further comprise sterilizing the one or more hydrolyzed proteins, the one or more disaccharides, the one or more oligosaccharides, and the one or more polysaccharides before step (a). The method may further comprise cutting, crushing, milling or pulverizing the composition into a free flowing powder. The particle size of the powder may be less than about 1000 μm.

In the method of the present invention, the composition may comprise an effective amount of the one or more viable probiotic microorganisms for providing a probiotic benefit to a host in a special dietary product. The method may further comprise making the special dietary product with the composition. The special dietary product may be selected from the group consisting of an infant formula, a follow-on formula, processed cereal based food, canned baby food, an animal supplement or treatment, and/or a special food for a medical purpose. In particular embodiments, the special dietary product is preferably an infant formula.

BRIEF DESCRIPTION OF THE DRAWINGS

FIG. 1 shows storage stability of samples of Example 2 under accelerated storage conditions of 40° C. and 33% RH.

DETAILED DESCRIPTION OF THE INVENTION

The present invention provides novel stable dry probiotic compositions, preferably for special dietary uses, and methods for making such compositions. These compositions provide desirable stability and protection to probiotic microorganisms. The probiotic microorganisms may be protected during manufacturing processes for making consumable products, through distribution channels, and under extreme storage conditions. Most probiotic formulators utilize in their products an extremely high count of bacterial cells, which may sometimes be as high as 10 and even 100 times more than an effective dose, with the understanding that a significant number of the cells ultimately lose viability and die during the manufacturing processes, transportation, and storage.

The term "special dietary use" as used herein refers to making or applying a special dietary product to a host. Preferably, the special dietary product is recommended by the joint FAO/WHO Codex Alimentarius Commission in a document entitled "Standard For Infant Formula and Formulas For Special Medical Purposes Intended for Infants, CODEX STAN 72-1981" ("US Standard Codex 72"). Examples of a special dietary product include an infant formula, a follow-on formula, processed cereal based food, canned baby food, and special food for a medical purpose. Preferably, the special dietary product is an infant formula.

The host may be any animal, including a fish, an avian, e.g., a chicken, or a mammal such as a ruminant, a pig, or a companion animal such as an equine, canine, or feline. In particular embodiments the mammal is a human. The human host may be an infant, a child or an elderly person. Preferably, the human host is an infant.

The term "infant" as used herein refers to a human from birth to about 12 months old.

The term "child" as used herein refers to a human from about 12 months old to about 12 years old. The term "elderly person" as used herein refers to a human at least about 55, 60, 65 or 70 years old, preferably at least about 65 years old.

The terms "probiotic microorganism" and "probiotic" are used herein interchangeably, and refer to a live microorganism that provides or confers a probiotic benefit to a host when administered to the host in an effective amount. The term "effective amount" as used herein refers to an amount of a probiotic microorganism that is sufficient to achieve a desirable probiotic benefit in a host when administered to the host via, for example, a dietary product such as a special dietary product. The probiotic microorganism may be selected from the group consisting of live probiotic bacteria, fungi, and yeast. The desirable probiotic benefit may be any beneficial health or nutritional effect, for example, maintaining a healthy gastrointestinal flora, enhancing immunity, preventing allergies and cold and protecting against diarrhea, atopic dermatitis and urinary infections.

The term "viability" as used herein refers to the ability of a probiotic microorganism in a composition to form colonies on a nutrient media appropriate for the growth of the probiotic microorganism, and may be expressed as colony forming units (CFU) over the weight of the composition, e.g., CFU/g.

The term "relative humidity (RH)" as used herein refers to the amount of water vapor in the air, often at a given temperature. Relative humidity is usually less than that is required to saturate the air, and is often expressed in percentage of saturation humidity.

The term "dry" as used herein refers to a physical state of a substance, for example, the composition of the present invention, that is dehydrated or anhydrous, e.g., substantially lacking liquid. The substance, for example, the composition of the present invention, may be dried by one or more drying processes, for example, air drying, vacuum drying, fluidized bed drying, spray drying, and lyophilization.

The term "water activity (Aw)" as used herein refers to the availability of water in a substance, for example, the composition of the present invention, which represents the energy status of water in the substance. It may be defined as the vapor pressure of water above a substance divided by that of pure water at the same temperature. Pure distilled water has a water activity of exactly one, i.e., Aw=1.0. A dry substance may have an Aw of about 0.5 or lower, preferably about 0.3 or lower, more preferably about 0.2 or lower, most preferably about 0.1 or lower.

A dry composition is provided. The composition comprises one or more viable probiotic microorganisms, one or more hydrolyzed proteins, one or more disaccharides, one or more oligosaccharides, and one or more polysaccharides. The composition has an initial viability of at least $1\times10^9$, $1\times10^{10}$, $1\times10^{11}$ or $1\times10^{12}$ CFU/g, preferably $1\times10^{10}$ CFU/g. The composition has a viability loss of less than 1 log unit/g after a predetermined period of time under predetermined conditions. Preferably, the composition does not comprise trehalose.

The composition may comprise an effective amount of the one or more viable probiotic microorganisms for providing a probiotic benefit to a host in a special dietary product. The special dietary product may be an infant formula, a follow-on formula, processed cereal based food, canned baby food, or special food for a medical purpose, preferably an infant formula.

The predetermined period of time may be about 1, 2, 3 or 4 weeks, or 1, 2, 3, 4, 5, 6, 12, 18, 24 or 36 months, preferably about 1, 2 or 3 months, more preferably 1 or 3 months. A specified time period may include a shorter or longer time period that is within 10% of the specified time period. The term "3 months" as used herein refers to a time period of about 84-90 days. The term "2 months" as used herein refers to a time period of about 56-60 days. The term "1 month" as used herein refers to a time period of about 28-30 days.

The predetermined conditions may include a predetermined temperature and a predetermined relative humidity (RH). The predetermined temperature may be at least about 25, 37, 40, 45, 50 or 55° C. The predetermined relative humidity (RH) may be at least about 10%, 20%, 30%, 33%, 35%, 40%, 50%, 60%, 70% or 80%.

The predetermined conditions may be accelerated storage conditions. For example, the predetermined conditions may include at least about 40° C. and at least about 33% RH, or at least about 45° C. and at least about 33% RH.

The composition may have a viability loss of less than 1 log unit/g after about 3 months at about 40° C. and 33% RH, or after 1 month at about 45° C. and 33% RH.

The composition may comprise about 1-30%, 10-25%, 10-20% or 15-20% of the one or more viable probiotic microorganisms, based on the total dry weight of the composition. Suitable probiotic microorganisms include, but are not limited to, yeasts such as *Saccharomyces, Debaromyces, Candida, Pichia* and *Torulopsis*; moulds such as *Aspergillus, Rhizopus, Mucor, Penicillium* and *Torulopsis*; and bacteria such as the genera *Bifidobacterium, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*. Specific examples of suitable probiotic microorganisms may be represented by the following species and include all culture biotypes within those species: *Aspergillus niger, A. oryzae, Bacillus coagulans, B. lentus, B. licheniformis, B. mesentericus, B. pumilus, B. subtilis, B. natto, Bacteroides amylophilus, Bac. capillosus, Bac. ruminocola, Bac. suis, Bifidobacterium adolescentis, B. animalis, B. breve, B. bifidum, B. infantis, B. lactis, B. longum, B. pseudolongum, B. thermophilum, Candida pintolepesii, Clostridium butyricum, Enterococcus cremoris, E. diacetylactis, E. faecium, E. intermedius, E. lactis, E. muntdii, E. thermophilus, Escherichia coli, Kluyveromyces fragilis, Lactobacillus acidophilus, L. alimentarius, L. amylovorus, L. crispatus, L. brevis, L. case L. curvatus, L. cellobiosus, L. delbrueckii ss. bulgaricus, L farciminis, L. fermentum, L. gasseri, L. helveticus, L. lactis, L. plantarum, L. johnsonii, L. reuteri, L. rhamnosus, L. sakei, L. salivarius, Leuconostoc mesenteroides, P. cereviseae (damnosus), Pediococcus acidilactici, P. pentosaceus, Propionibacterium freudenreichii, Prop. shermanii, Saccharomyces cereviseae, Staphylococcus carnosus, Staph. xylosus, Streptococcus infantarius, Strep. salivarius. thermophilus, Strep. Thermophilus* and *Strep. Lactis*. Preferably, the probiotics are lactic acid bacteria and bifido bacteria.

The composition may comprise at least about 40% or 50%, preferably at least about 50% of the one or more hydrolyzed proteins, based on the total dry weight of the composition. For example, the composition may comprise about 40-80%, 40-70%, 50-70% or 50-60%, preferably 40-80%, of the hydrolyzed protein.

The terms "hydrolyzed protein" and "protein hydrolysate" are used herein interchangeably, and refer to proteins broken down by hydrolysis or digestion into shorter peptide fragments and/or amino acids. The hydrolysis or digestion may be carried out by a strong acid, a strong base, an enzyme or a combination thereof. The hydrolyzed protein may be from an animal or a plant, preferably from a mammal, more preferably from a dairy source. The hydrolyzed proteins may be milk proteins, plant proteins, or a mixture thereof.

The hydrolyzed protein may be partially or extensively hydrolyzed, preferably extensively hydrolyzed. The hydrolyzed protein may be a mixture of polypeptides and amino acids. In some embodiments, at least about 60%, 70%, 80%, 90%, 95% or 99%, preferably at least about 70%, of the hydrolyzed protein has a molecular weight lower than about 100,000, 75,000, 50,000, 25,000, 10,000, 5,000, 1,000 or 500 Dalton, preferably about 50,000 Dalton, more preferably about 10,000 Dalton, more preferably about 2,000 Dalton. For example, at least about 50%, 60%, 70%, 80% or 90%, preferably at least about 70%, of the hydrolyzed protein has a molecular weight lower than about 2,000 Daltons.

Proteins suitable for making hydrolyzed proteins for the composition of the present invention include egg proteins, gelatin, milk proteins, casein, whey protein, albumen, soy protein, pea protein, rice protein, wheat protein, and other plant proteins. Preferably, the proteins are those recommended for special dietary uses.

Examples of the hydrolyzed proteins include hydrolyzed casein, hydrolyzed whey protein, hydrolyzed pea protein, hydrolyzed soy protein, and combinations thereof. In one preferred embodiment, the hydrolyzed protein comprises hydrolyzed casein or pea proteins, at least about 80% of which has a molecular weight of less than about 2,000 Daltons.

The composition comprises a carbohydrate mixture of disaccharides, oligosaccharides and polysaccharides, in which the probiotic microorganism is embedded. Without being bound by theory, it is believed that a matrix formed by combining a carbohydrate mixture and extensively hydrolyzed proteins as described herein allows faster drying and contributes to a desirable amorphous and rigid structure of the resulting dry composition.

The composition may comprise less than about 30%, 20% or 10%, preferably less than 20%, of the one or more disaccharides, based on the total dry weight of the composition. For example, the composition may comprise about 1-30%, 1-20%, 1-10%, 5-30%, 5-20%, 5-10%, 10-20%, 10-15% or 10-20%, preferably about 5-30%, of the disaccharide.

The disaccharides are preferably those recommended for special dietary uses. The disaccharide may be lactose, sucrose, maltose, fructose, or a combination thereof, preferably lactose or sucrose, more preferably lactose. The disaccharide is preferably not trehalose. In some preferred embodiments, the composition of the invention does not comprise trehalose.

The composition may comprise about 1-30%, 1-20%, 1-10%, 5-30%, 5-20%, 5-10%, 10-20%, 10-15% or 10-20% of the one or more oligosaccharides, based on the total dry weight of the composition. Preferably, the composition comprises 5-30% of the oligosaccharides.

Oligosaccharides are soluble fibers often considered as prebiotics in nutritional applications. Advantageously, soluble fibers pass through the stomach undigested and become available for digestion by the gut microflora. The incorporation of soluble fibers may also help to protect the probiotic from digestive enzymes and high acidity of the stomach.

The oligosaccharides are preferably those recommended for special dietary uses. The oligosaccharide may be inulin, maltodextrin, dextran, fructo-oligosaccharide (FOS), galacto-oligosaccharide (GOS), mannan-oligosaccharide (MOS), or a combination thereof, preferably maltodextrin or inulin, more preferably inulin.

The composition may comprise about 0.1-40%, 0.5-30%, 1-30%, 1-20%, 1-10%, 1-5% or 5-10% of the one or more polysaccharides, based on the total dry weight of the composition. Preferably, the composition comprises 1-10% of the polysaccharide. The polysaccharides are preferably those recommended for special dietary uses. The polysaccharide may be carrageenan, guar gum, gum acacia, locust bean gum, starch, modified starch, or a combination thereof, preferably locust bean gum or guar gum, more preferably locust bean gum. Preferably, the polysaccharide is not alginate or chitosan. In some preferred embodiments, the composition does not comprise alginate or chitosan. In some other preferred embodiments, the composition does not comprise trehalose or alginate.

In some embodiments, the composition comprises 0.1-20% of polysaccharides, 5-30% of oligosaccharides, and 1-20% of disaccharides, on the total dry weight of the composition. In particular, the composition may comprise 0.1-20% of locust bean gum, 5-30% of Inulin and 1-20% lactose, based on the total dry weight of the composition.

The composition of the present invention may further comprise one or more additional agents. The additional agent may provide an additional benefit to the probiotic microorganism, the host or both. For example, the additional agent may provide a therapeutic or immunogenic effect to the host. The addition agent may be selected from the group consisting of vitamins, antioxidants, trace elements, sterols, magnesium stearate, fumed silica, surfactants, peptides and steroids and combinations thereof.

The composition may comprise 0.1-20%, 0.5-20%, 1-20%, 0.1-10%, 0.5-10%, 1-10% or 1-5% of the additional agent, based on the total weight of the composition. The additional agent is preferably an agent recommended for special dietary uses.

The additional agent may be selected from the group consisting of carboxylic acid salts, tocopherols, and combinations thereof. The carboxylic acid salts may be selected from the group consisting of ascorbic acid salts and citric acid salts. In some embodiments, the additional agent comprises one or more tocopherols and one or more carboxylic acid salts at a weight ratio from 4:1 to 1:4. For example, the additional agent comprises vitamin E and sodium ascorbate at a weight ratio of 4:1.

In some embodiments, the composition comprises 40-80% hydrolyzed proteins, 5-30% disaccharides, 5-30% oligosaccharides and 1-10% polysaccharides, based on the total weight of the composition. In a preferred embodiment, the composition comprises 54% of hydrolyzed pea protein, 8% lactose, 14% inulin and 3% locust bean gum, based on the total weight of the composition. The composition may further comprise 4% of an additional agent comprising vitamin E and sodium ascorbate at a weight ratio of 4:1, based on the total weight of the composition.

The composition of the present invention may be prepared by techniques known in the art. The preparation method may include processes such as mixing, freezing, freeze-drying, ambient air drying, vacuum drying, spray drying, or a combination thereof. The resulting probiotic composition, whether alone or integrated into a special dietary product, possesses enhanced viability when exposed to a wide range of temperatures and humidity conditions.

The probiotic microorganism used to prepare the composition is preferably a fermentation harvest that is concentrated to a wet paste-like consistency having a solid content of about 5-30% w/v. The probiotic concentrate can be in a form of wet, frozen or thawed paste before being combined with other ingredients. Starting with a probiotic microorganism in a dry form is an alternative.

The preparation of a stable probiotic composition may include concentrating a selected probiotic, mixing ingredients with the concentrated probiotic to form a slurry, snap-freezing the slurry in liquid nitrogen to form particles in the form of droplets, strings or beads, drying the particles by evaporating the moisture in the particles under a regimen of reduced pressure while supplying heat to the particles, and then packaging or combining the resulting stable probiotic composition into a special dietary product, which may be a nutritional product such as an infant formula.

One suitable mixing process may be adding a dry mixture of all ingredients except the probiotic microorganism in the composition directly into a concentrate culture or media solution comprising the probiotic microorganism to form a slurry. The dry mixture may be pre-dissolved in a water solution adjusted to pH of 8-9 with a concentrated alkali solution (e.g., 1M or 5M sodium hydroxide (NaOH) solution) at 20-80° C. In the slurry, the dry weight mass of the probiotic microorganism may constitute about 5-30% w/v while the dry mixture may constitute about 70-95% or 80-90% w/v. The total solid content in the slurry may be about 20-60% or 30-50%. The amount of polysaccharides in the dry mixture may be adjusted to achieve a desired viscosity of the slurry allowing efficient drying while avoiding rubbery formation or excessive foaming that may occur during drying. A desirable density of the slurry may be achieved by any means known in the art, for example, by degassing under vacuum or injecting gas such as air, nitrogen, carbon dioxide, or argon.

The slurry may be snap-frozen to from about −30° C. to about −180° C., or snap-frozen in liquid nitrogen by atomizing, dripping or injecting into a liquid nitrogen bath. The resulting particles in the form of beads, strings or droplets may be collected and dried in a freeze drier or vacuum drier, or alternatively stored in a deep freezer (e.g., between −30° C. and −80° C.) for later use in a frozen form or for later drying, e.g., by freeze drying or vacuum drying.

In general, the drying process techniques that are useful include freeze drying, or evaporative drying of a thawed slurry in a vacuum oven or centrifugal evaporator while the temperature of the slurry or the drying product is maintained above its freezing temperature (e.g., −20 to −5° C.), followed by milling to desirable particle size. Preferably, the probiotic microorganism is coated by non-crystallized amorphous materials in the particles. The advantage of coating the probiotic microorganism with materials in an amorphous state is to increase physical stability of the particles and reduce deleterious crystalline formation within the particles. It should be noted that achieving a non-crystallized amorphous structure is not a prerequisite for long term stability as some microorganisms may fare better in a more crystalline state. In a suitable exemplary embodiment, the snap-frozen slurry may be loaded onto trays at a loading capacity from about 0.1 kg/sqft to about 1.5 kg/sqft and then immediately transferred to a vacuum drying chamber where the drying process may proceed in three major steps including: (a) an optional short temperature acclimation and structure stabilizing step of the frozen particles under a vacuum pressure of less than <1000 mTORR, (b) primary drying, or primary evaporative drying, under vacuum and at a temperature of the particles above their freezing point, and (c) secondary drying under full strength vacuum pressure and an elevated heat source temperature for a time sufficient to reduce the water activity of the resulting dry composition to, for example, 0.3 Aw or less. The resulting dry composition may be glassy amorphous.

The terms "lyophilization" and "freeze drying" are used herein interchangeably and refer to the preparation of a composition in dry form by rapid freezing and dehydration in the frozen state (sometimes referred to as sublimation). Lyophilization takes place at a temperature that results in the crystallization of ingredients in the composition.

The term "primary drying" as used herein refers to drying a product at a temperature of the product substantially lower than the temperature of a heat source, i.e., heat source temperature or shelf temperature, to make a primarily dried product. Typically, the bulk of primary drying may be carried out by extensive evaporation, while the product temperature remains significantly lower than the temperature of the heat source.

The term "secondary drying" as used herein refers to drying a primarily dried product at a temperature of the product near the temperature of a heat source, i.e., heat source temperature or shelf temperature, to make a dry product. This process may take place under vacuum sufficient to reduce the water activity of the resulting dry product. In a typical drying process, a secondary drying step reduces the water activity of the formulation to, for example, an Aw of 0.3 or less.

In one embodiment, the composition of the present invention is prepared by a method comprising (a) combining one or more viable probiotic microorganisms, one or more hydrolyzed proteins, one or more disaccharides, one or more oligosaccharides, and one or more polysaccharides in an alkali aqueous solvent to form a slurry; (b) snap-freezing the slurry in liquid nitrogen to form solid frozen particles in the form of beads, droplets or strings; (c) primary drying step of the solid frozen particles by evaporation, under vacuum, while the temperature of the particles is maintained above their freezing temperature, whereby a primarily dried formulation is formed; and (d) secondary drying of the primarily dried formulation at full strength vacuum and a heat source temperature of 20° C. or higher for a time sufficient to reduce the water activity of the primarily dried formulation to 0.3 Aw or lower, whereby the composition is prepared.

The method may further comprise sterilizing the one or more hydrolyzed proteins, the one or more disaccharides, the one or more oligosaccharides and the one or more polysaccharides before step (a). The sterilization may be achieved by any method known in the art. For example, heating under pressure a mixture of the hydrolyzed protein, the disaccharide, the oligosaccharide and the polysaccharide, and followed by cooling before step (a).

The method may further comprise solubilizing the one or more hydrolyzed proteins, the one or more disaccharides, the one or more oligosaccharides and the one or more polysaccharides before step (a).

The method may further comprise cutting, crushing, milling or pulverizing the composition into a free flowing powder. The particle size of the powder may be less than about 10,000, 1,000, 500, 250 or 100 µm, preferably less than about 1,000 µm, more preferably less than about 250 µm.

The dry composition of the present invention may be used directly as a flake, or grounded into a powder and sieved to an average particle size from about 1-10,000 µm, preferably 10-1,000 µm.

The composition of the present invention may be administrated as a concentrated powder or a reconstituted liquid (e.g., a beverage). It may also be incorporated either in flake or powder form into an existing food product.

The method may further comprise making a special dietary product with the composition of the present invention, which comprises an effective amount of the one or more viable probiotic microorganisms for providing a probiotic benefit to a host in the special dietary product. Examples of the special dietary product may include an infant formula, a follow-on formula, processed cereal based food, canned baby food, and special food for a medical purpose. Preferably, the special dietary product is an infant formula.

The resulting dry stable powder comprising probiotics may be agglomerated with molten fats. The dry powder may be placed in a planetary mixer at 40° C. and molten fats such as cocoa butter, natural waxes or palm oil, stearic acid, stearine or a mixture thereof may be added slowly to the warm powder. The mixture may be cooled down to below the melting temperature of the fats while mixing continues until a visually uniform size of agglomerated powder is achieved. The weight mass of the molten fats in the resulting composition may be about 20-70%, preferably 30-50%.

EXAMPLE 1

Preparation of Dry and Stable Composition

Hydrolyzed pea protein (65 g, Marcor, Carlstadt, N.J.) was dissolved in 100 ml warm distilled water (75° C.). The pH of the pea solution was adjusted to 8.5 using a 20% concentrated NaOH solution. Locust Bean gum (3 g, Tic gum, Belcamp, Md.), lactose (10 g, Foremost Farms, Rothschild, Wis.), Inulin (17 g, Cargill Minneapolis, Minn.), a mixture of vitamin E and sodium ascorbate at 4:1 w/w (5 g) were dry blended and added to the pea solution under continuous mixing at 500 rpm with an impeller mixer. The solution was cooled down and maintained at a temperature between 35° C. and 40° C. under continuous mixing.

This resulted stabilizing composition was translucent with a consistency of syrup and amber in color. The syrupy solution was transferred to a dual planetary mixer (DPM, 1 qt, Ross Engineering, Inc. Savannah, Ga.) equipped with controlled temperature jacket. The mixer jacket temperature was 37° C. Frozen bacteria (100 g, *Bifidobacterium* sp.) were added under mixing at 45 rpm for 2-3 minutes, or until all the bacteria were well thawed and homogenously distributed. The probiotic mixture was cooled down to 4° C. and kept at this temperature for 30-60 minutes. The mixture was dripped and snap-frozen in a liquid nitrogen bath to form frozen beads, where were harvested from the liquid nitrogen and stored at −80° C. for later drying.

For drying, the frozen beads were spread on pre-cooled trays (−20° C.) at a loading capacity of 800 g/sqft and then immediately placed on shelves in a freeze drier (Model 25 SRC, Virtis, Gardiner, N.Y.). Vacuum was then adjusted to between 1800-2200 mTORR and the shelf temperature was raised to +20° C. These temperature and vacuum pressure settings were maintained for 12 hours. Before primary drying, the temperature of the frozen beads was optionally acclimatized to about −20° C. by applying a vacuum pressure at about 1000 mTORR to allow the temperature of the frozen beads to acclimate for about 10 minutes. The primary drying step was then followed by adjusting the vacuum pressure to 2000-2700 mTORR and the shelf temperature to +20° C. These temperature and vacuum pressure settings were maintained for 12 hours. A secondary drying step was then followed at full strength vacuum (150-200 mTORR) and the shelf temperature was maintained at 40° C. for additional 12 hours. The formulation was completely dried and its water activity as measured by a Hygropalm Aw1 instrument (Rotonic Instrument Corp., Huntington, N.Y.) was Aw 0.23. The dry material was then milled and (sieved to particle size ≤250 μm and stored at 4° C.

EXAMPLE 2

Storage of Stability of the Dry Probiotic Composition

Samples comprising the dry stable composition of probiotic bacteria from Example 1 or commonly freeze dried bacteria suspension in 10% trehalose were placed in a desiccator under accelerated storage conditions of 40° C. and 33% RH. Samples were taken periodically for microbial CFU assessment using standard microbiological dilutions and LMRS agar plating procedures. FIG. 1 shows the storage stability under accelerated storage conditions of 40° C. and 33% RH. The unprotected probiotic bacteria completely lost its viability within the first few weeks under the accelerated storage conditions, while the dry composition of the probiotic bacteria of the present invention lost only 0.70 log unit/g after 84 days at 40° C. and 33% RH.

EXAMPLE 3

Effects of Carbohydrates and Proteins on Storage Stability

The compositions of the present invention eliminates the need for those carbohydrate stabilizers that are not included in the recommended list of nutritional compounds allowed for special dietary uses, according to the joint FAO/WHO Codex Alimentarius Commission.

a. A composition comprising Maltodextrin: A composition containing 50 g pea protein hydrolysate (Marcor, Carlstadt, N.J.) 33 g maltodextrin (Tate & Lyle, Decatur, Ill.) 10 g inulin (Cargill, Minneapolis, Minn.), 2 g Locust Bean gum (Tic gum, Belcamp, Md.) and 5 g mixture of vitamin E and sodium ascorbate (4:1 w/w) was prepared. The Pea protein hydrolysate dissolved in 100 grams of distilled water and pH adjusted to 7.5. The carbohydrate compounds were dry blended and Added to the pea protein solution. The mixture was heated to 70° C. to dissolve all the compounds and the solution cooled down to 37° C. Frozen beads of *L. rhamnosus* sp. (100 g) were added to the solution and the slurry dried as described in Example 1. The initial count of live bacteria in the dry composition was 9.92 log CFU/g. A sample of this product was placed under accelerated stability challenge as described in Example 1. The sample had 1.19 log unit/g loss after 1 month thus, failed the challenge.

b. A composition comprising Wheat protein isolate: Another composition comprising 25 g pea protein hydrolysate (Marcor, Carlstadt, N.J.), 33 g Prolite 200 (wheat protein isolate, Archer Daniels Midland Company Decatur, Ill.) 25 g maltodextrin (Tate & Lyle, Decatur, Ill.) 10 g inulin (Cargill, Minneapolis, Minn.), 2 g Locust Bean gum (Tic gum, Belcamp, Md.) and 5 g mixture of vitamin E and sodium ascorbate (4:1 w/w) was prepared. A composition containing *L. rhamnosus* sp. was prepared and dried as described above in Examples 1 and 2. The initial count of live bacteria in the dry composition was 10.17 log CFU/g. A sample of this product was placed under accelerated stability challenge as described in Example 1, The sample resulted 1.71 log unit/g loss after two weeks thus, failed the challenge test.

c. A composition comprising Whey protein isolate: Another composition containing 25 g pea protein hydrolysate (Marcor, Carlstadt, N.J.), 25 g whey protein isolate (Davisco, Eden Prairie, Minn.), 33 g maltodextrin (Tate & Lyle, Decatur, Ill.) 10 g inulin (Cargill, Minneapolis, Minn.), 2 g Locust Bean gum (Tic gum, Belcamp, Md.) and 5 g mixture of vitamin E and sodium ascorbate (4:1 w/w) was prepared. A composition containing *L. rhamnosus* sp. was prepared and dried as described above in Examples 1 and 2. The initial count of live bacteria in the dry composition was 10.40 log CFU/g. A sample of this product was placed under accelerated stability challenge as described in Example 1. The sample resulted 1.30 log unit/g loss after two weeks thus, failed the challenge test.

d. A composition comprising lactose: Another composition containing 50 g pea protein hydrolysate (Marcor, Carlstadt, N.J.) 33 g lactose (Foremost Farms, Rothschild, Wis.) 10 g inulin (Cargill, Minneapolis, Minn.), 2 g Locust Bean gum (Tic gum, Belcamp, Md.) and 5 g mixture of vitamin E and sodium ascorbate (4:1 w/w) was prepared. A composition containing *L. rhamnosus* sp. was prepared and dried as described above in Examples 1 and 2. The initial count of live bacteria in the dry composition was 9.77 log CFU/g. A sample of this product was placed under accelerated stability challenge as described in Example 1. The sample passed the first month stability but had 1.89 log unit/g loss after 2 months thus, failed the challenge test.

e. The composition of the present invention: A composition containing 65 g pea protein hydrolysate (Marcor, Carlstadt, N.J.) 10 g lactose (Foremost Farms, Rothschild, Wis.) 17 g inulin (Cargill, Minneapolis, Minn.), 3 g Locust Bean gum (Tic gum, Belcamp, Md.) and 5 g mixture of vitamin E and sodium ascorbate (4:1 w/w) was prepared. A composition containing *Bifidobacterium* sp. was prepared and dried as described above in Examples 1 and 2, except that the pH of pea protein hydrolysate solution adjusted to pH 8.5. The initial count of live bacteria in the dry composition was 10.87 log CFU/g. A sample of this product was placed under accelerated stability challenge. The sample lost only 0.70 log unit/g after 3 months, thus, passed the challenge test.

EXAMPLE 4

Effects of Inulin on Storage Stability

US Standard codex 72 allows the use of oligosaccharides such as inulin and maltodextrin in infant formula. The effect of inulin levels from 0% to 30% in the composition was evaluated. Compositions containing 50 g pea protein hydrolysate (Marcor, Carlstadt, N.J.), 43 g lactose (Foremost Farms, Rothschild, Wis.), 2 g Locust Bean gum (Tic gum, Belcamp, Md.), 5 g mixture of vitamin E and sodium ascorbate (4:1 w/w), and 0 g, 10 g, 15 g or 30 g of inulin were prepared (the added amount of inulin was subtracted from the amount of lactose in the composition). The compositions containing *L. acidophilus* sp. were prepared and dried as described above in Examples 1 and 2. The initial counts of live bacteria in the dry compositions comprising 0 g, 10 g, 15 g, and 30 g inulin was 9.42, 9.57, 9.59 and 9.80 log CFU/g, respectively. A sample from each composition was placed under accelerated stability challenge. The sample comprising 0 g inulin (no oligosaccharides) lost 1.14 log unit/g after 2 months and 2.25 log unit/g after 3 months while samples comprising 15 g and higher inulin lost less than 2 log unit/g after 3 months, thus, it was determined that the minimal amount of inulin in the composition of the current invention must be higher than 10%.

EXAMPLE 5

Effects of Disaccharides on Storage Stability

US Standard codex 72 restricts the use of trehalose but allows the use of sucrose and lactose in infant formula. The following example demonstrates that trehalose was successfully replaced with an increased amount of hydrolyzed pea protein and only small amount of the disaccharide lactose according to the composition of the current invention.

a. A composition comprising trehalose: A composition containing 25 g pea protein hydrolysate (Marcor, Carlstadt, N.J.) 62 g trehalose (Cargill, Minneapolis, Minn.) 5 g inulin (Cargill, Minneapolis, Minn.), 3 g Locust Bean gum (Tic gum, Belcamp, Md.) and 5 g mixture of vitamin E and sodium ascorbate (4:1 w/w) was prepared. A composition containing *L. acidophilus* sp. was prepared and dried as described above in Examples 1 and 2. The initial counts of live bacteria in the dry composition was 9.49 log CFU/g. A sample of the composition was placed under accelerated stability challenge. The sample lost 0.83 log unit/g after 3 months thus, demonstrating a relatively good stability. Nevertheless, the use of trehalose is not allowed in infant formula.

b. Effect of trehalose replacement with lactose: Compositions containing 50 g pea protein hydrolysate (Marcor, Carlstadt, N.J.), 2 g Locust Bean gum (Tic gum, Belcamp, Md.), 5 g mixture of vitamin E and sodium ascorbate (4:1 w/w)and 33 g lactose (Foremost Farms, Rothschild, Wis.), 10 g inulin (Cargill, Minneapolis, Minn.) or 13 g and 30 g inulin were prepared. The compositions containing *L. acidophilus* sp. were prepared and dried as described above in Examples 1 and 2. The initial counts of live bacteria in the dry compositions comprising 33 g or 13 g lactose were 9.57 log CFU/g and 9.80 log CFU/g, respectively. A sample from each composition was placed under accelerated stability challenge. The sample comprising 33 g lactose lost 1.25 log unit/g after 1 month while the sample comprising 13 g lactose last for 2 months, thus, it was determined that 13% of lactose and accompanied with 50% of hydrolyzed pea protein in the stabilizing composition can effectively replace trehalose.

c. Stability of compositions without trehalose and alginate: To evaluate the effect of replacement of ingredients (e.g., trehalose and alginate) not desirable for an infant formula in compositions having over 50% disaccharides, three (3) compositions containing 25 g pea protein hydrolysate (Marcor, Carlstadt, N.J.), 5 g inulin (Cargill, Minneapolis, Minn.), 5 g mixture of vitamin E and sodium ascorbate (4:1 w/w), 3 g alginate (ISP Corp., Wayne, N.J.) or 3 g Locust Bean gum (Tic gum, Belcamp, Md.), and 62 g trehalose (Cargill, Minneapolis, MN) or 62 g lactose (Foremost Farms, Rothschild, Wis.) were prepared (Table 1). Compositions containing *L. rhamnosus* sp. were prepared and dried as described above in Examples 1 and 2. The initial counts of live bacteria in the three dry compositions were about 10 log CFU/g (Table 1). A sample from each composition was subject to accelerated stability challenge. Only the composition comprising both alginate and trehalose demonstrated less than 1 log unit/g loss after 84 days, while the other two compositions, in which trehalose and alginate were replaced with lactose and locust bean gum, respectively, lost more than a log unit/g after only 28 days. Thus, trehalose and alginate are essential ingredients in compositions, which typically have over 50% disaccharides, for achieving the stability requirement of less than 1 log unit/g loss after 3 months at 40° C. and 33% relative humidity.

TABLE 1

Effect of trehalose and alginate replacement on probiotic stability

| Composition | 1 | 2 | 3 |
|---|---|---|---|
| Pea protein hydrolysate | 25 g | 25 g | 25 g |
| Trehalose | 62 g | 0 | 0 |
| Lactose | 0 | 62 g | 62 g |
| Inulin | 5 g | 5 g | 5 g |
| Alginate | 3 g | 3 g | 0 |
| Locust bean gum | 0 | 0 | 3 g |
| Vitamin mixture | 5 g | 5 g | 5 g |
| Initial viability (log CFU/g) | 10.08 | 9.84 | 10.16 |
| Viability loss (log CFU/g/days) | 0.96/84 | 1.24/28 | 1.62/28 |

EXAMPLE 6

Effects of Polysaccharides on Storage Stability

Polysaccharide provides structural support that is essential in the probiotic composition. US Standard codex 72 restricts the use of several polysaccharides such as alginate but allows the use of guar gum, locust bean gum and starch in infant formula. Sodium alginate, guar gum, locust bean gum, and starch are commercially available polysaccharides and their effect in the stabilizing composition of the present invention was evaluated.

a. A composition comprising guar gum: A composition containing 36 g casein hydrolysate (DMV International Nutritionals, Delhi, N.Y.) 25 g inulin (Cargill, Minneapolis, Minn.) 36 g sucrose (Sigma), and 3 g guar gum (Tic gum, Belcamp, Md.) was prepared. A composition containing *L. rhamnosus* sp. was prepared and dried as described above in Examples 1 and 2. The initial count of live bacteria in the dry composition was 9.90 log CFU/g. A sample of this product was placed under accelerated stability challenge as described in Example 1. The sample passed the first month stability but had 1.10 log unit/g loss after 2 months thus, failed the challenge test.

b. A composition comprising sodium alginate: A composition containing 17 g casein hydrolysate (DMV International Nutritionals, Delhi, N.Y.) 5 g inulin (Cargill, Minneapolis, Minn.) 75 g sucrose (Sigma), and 3 g sodium alginate (ISP Corp., Wayne, N.J.) was prepared. A composition containing *L. rhamnosus* sp. was prepared and dried as described above in Examples 1 and 2. The initial count of live bacteria in the dry composition was 9.90 log CFU/g. A sample of this product was placed under accelerated stability challenge as described in Example 1. The sample passed the first month stability but had 1.25 log unit/g loss after 2 months thus, failed the challenge test.

c. A composition comprising locust bean gum: A composition containing 25 g pea protein hydrolysate (Marcor, Carlstadt, N.J.), 5 g inulin (Cargill, Minneapolis, Minn.), 62 g trehalose (Cargill, Minneapolis, Minn.), 3 g locust bean gum (Tic Gums, Belcamp, Md.) and 5 g mixture of vitamin E and sodium ascorbate (4:1 w/w) was prepared. A composition containing *L. rhamnosus* sp. was prepared and dried as described above in Examples 1 and 2. The initial count of live bacteria in the dry composition was 9.93 log CFU/g. A sample of this product was placed under accelerated stability challenge as described in Example 1. The sample passed the 2 month stability with 0.81 log unit/g loss. It was determined that locust bean gum can replace the alginate functionality in stabilized probiotic compositions.

EXAMPLE 7

Infant Formula

A stable dry composition comprising *Bifidobacterium* sp. was prepared according to Example 1 followed by sieving into two particle size groups (above 50 µm and below 250 µm). An infant formula comprising probiotic bacteria was prepared by mixing 99.9 g of Gerber Good Start (Nestle Infant Nutrition, Florham Park, N.J.) with 0.1 g of the dry composition particles in the size range between 50 µm and 250 µm). The final product contains about $10^8$ CFU of *Lactobacillus* GG per 100 g infant formula. The probiotic infant formula were packed into 180 cc HDPE bottles of and exposed to controlled temperature/humidity of 40° C./33% RH. The product is subjected to monthly microbiological stability testing over a period of 12 months or until a reduction in the assay count below $5\times10^7$/unit dose is observed.

EXAMPLE 8

Probiotic Supplement

A stable dry composition comprising *Lactobacillus acidophilus* is prepared according to Example 1 and formulated into oral dosage forms, such as tablets, caplets, or capsules. Orange flavored tablets containing 99.9 g of a compression agent (dextrose) and 0.1 g of the dry formulation particles in the size range between 50 µm and 250 µm are prepared by direct compression on a rotary machine using a ½" round standard concave tooling. The final product contains about $10^8$ CFU/unit dose. Hardness of the tablets is in the range of 8-10 kp and disintegration times is approximately 20 second. The compressed tablets are packaged into 180 cc HDPE bottles of 100 tablets each and exposed to controlled temperature/humidity of 40° C./33% RH. The product is subjected to monthly microbiological stability testing over a period of 12 months or until a reduction in the assay count below $1\times10^6$/unit dose is observed.

EXAMPLE 9

A Functional Beverage Drink

A stable dry composition comprising *Lactobacillus acidophilus* is prepared according to Example 1 and formulated into a dry mix containing (% by weight) 71% sucrose, 14% maltodextrin, 10% inulin, 2% dextrose, 1% citric acid anhydrous, 0.3% gum acacia, 0.3% flavors, 0.3% Tricalcium phosphate and 0.1% dry probiotic composition particles (*L. acidophilus*) in the size range between 50 µm and 250 µm. The final product contains about $10^9$ cfu/unit dose (30 g dry mix). The product is packaged in small aluminum foil bags (30 g unit dose/bag) for drinking by stirring in 340 mil water. The stability of the probiotic bacteria in the beverage dry mix is subjected to monthly microbiological stability testing over a period of 12 months or until a reduction in the assay count below $1\times10^7$/unit dose is observed.

EXAMPLE 10

Multivitamins/Probiotic Tablets

Ten (10) g of dry powder composition is produced as described in Example 1. For tableting, the dry and stable probiotic composition (100 mg) is mixed with 400 mg of commercially available multivitamins powder (Centrum®, Pfizer) containing 2% w/w magnesium stearate and 2% w/w hydrophilic fumed silica (AEROSIL® 200, Evonik Industries) and compressed in hand held pill press equipment (using a ½" tablet diameter housing). Each tablet contains about $10^7$ cfu/tablet). The tablets are packaged into 180 cc HDPE bottles of 100 tablets each and exposed to controlled temperature/humidity of 40° C./33% RH. The bottles are subjected to monthly microbiological stability testing over a period of 12 months or until a reduction in the assay count below $1\times10^6$/tablet is observed.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A dry composition comprising one or more viable probiotic bacteria, 65% of one or more hydrolyzed proteins, 10% of one or more disaccharides, 5-30% of one or more oligosaccharides, and 1-10% of one or more polysaccharides, wherein the one or more disaccharides are selected from the group consisting of sucrose, lactose and a combination thereof, wherein the one or more oligosaccharides are selected from the group consisting of inulin, maltodextrins, dextrans, fructo-oligosaccharides (FOS), galactooligosaccharides (GOS), mannan-oligosaccharides (MOS), and combinations thereof, wherein the one or more polysaccharides are selected from the group consisting of carrageenan, guar gum, gum acacia, locust bean gum, starches, modified starches, and combinations thereof, and wherein the one or more hydrolyzed proteins are selected from the group consisting of hydrolyzed casein, hydrolyzed whey protein, hydrolyzed pea protein, hydrolyzed soy protein, and combinations thereof, wherein the one or more probiotic bacteria in the composition have a viability of at least $1 \times 10^{10}$ CFU/g, and wherein the one or more probiotic bacteria in the composition have a viability loss of less than 1 log unit/g after 3 months at a temperature of 40° C. and a relative humidity of 33%.

2. The composition of claim 1, wherein the composition provides a probiotic benefit to a host in a special dietary product.

3. The composition of claim 2, wherein the special dietary product is selected from the group consisting of an infant formula, a follow-on formula, processed cereal based food, canned baby food, and special food for a medical purpose.

4. The composition of claim 2, wherein the special dietary product is an infant formula.

5. The composition of claim 1, wherein the probiotic bacteria are selected from the group consisting of *Bifidobacterium* spp, *Lactobacillus* spp and combinations thereof.

6. The composition of claim 1, further comprising one or more additional agents.

7. The composition of claim 6, wherein the composition comprises 0.5-10% of the one or more additional agents, based on the total weight of the composition.

8. The composition of claim 6, wherein the one or more additional agents are selected from the group consisting of carboxylic acid salts, tocopherols, and combinations thereof.

9. The composition of claim 8, wherein the carboxylic acid salts are selected from the group consisting of ascorbic acid salts and citric acid salts.

10. The composition of claim 6, wherein the one or more additional agents comprise one or more tocopherols and one or more carboxylic acid salts at a weight ratio from 1:4 to 4:1.

11. The composition of claim 6, wherein the one or more additional agents comprise vitamin E and sodium ascorbate at a weight ratio of 4:1.

12. A method for preparing the composition of claim 1, comprising one or more drying processes selected from the group consisting of air drying, vacuum-drying, fluid bed drying and spray-drying.

13. A method for preparing the composition of claim 1, comprising:

(a) combining the one or more viable probiotic microorganisms, the one or more hydrolyzed proteins, the one or more disaccharides, the one or more oligosaccharide, and the one or more polysaccharides in an alkali aqueous solvent to form a slurry;

(b) snap-freezing the slurry in liquid nitrogen to form solid frozen particles in the form of beads, droplets or strings;

(c) primary drying step of the solid frozen particles by evaporation, under vacuum, while maintaining the temperature of the particles above their freezing temperature, whereby a primarily dried formulation is formed; and (d) secondary drying of the primarily dried formulation at full strength vacuum and a heat source temperature of 20° C. or higher for a time sufficient to reduce the water activity of the primarily dried formulation to 0.3 Aw or lower, whereby the composition of claim 1 is prepared.

14. The method of claim 13, further comprising sterilizing the one or more hydrolyzed proteins, the one or more disaccharides, the one or more oligosaccharides, and the one or more polysaccharides before step (a).

15. The method of claim 13, further comprising cutting, crushing, milling or pulverizing the composition into a free flowing powder.

16. The method of claim 15, wherein the particle size of the powder is less than about 1000 μm.

17. The method of claim 13, wherein the composition comprises an effective amount of the one or more viable probiotic microorganisms for providing a probiotic benefit to a host in a special dietary product.

18. The method of claim 17, further comprising making the special dietary product with the composition.

19. The method of claim 17, wherein the special dietary product is selected from the group consisting of an infant formula, a follow-on formula, processed cereal based food, canned baby food, and special food for a medical purpose.

20. The method of claim 17, wherein the special dietary product is an infant formula.

21. The composition of claim 1, wherein the one or more disaccharides consist of lactose, wherein the one or more oligosaccharides consist of inulin, wherein the one or more polysaccharides consist of locust bean gum, and wherein the one or more hydrolyzed proteins consist of hydrolyzed pea protein.

* * * * *